United States Patent [19]

Rabbani et al.

[11] Patent Number: 4,755,458

[45] Date of Patent: Jul. 5, 1988

[54] COMPOSITION AND METHOD FOR THE DETECTION OF THE PRESENCE OF A POLYNUCLEOTIDE SEQUENCE OF INTEREST

[75] Inventors: Elazar Rabbani; Dean L. Engelhardt, both of New York, N.Y.

[73] Assignee: Enzo Biochem, Inc., New York, N.Y.

[21] Appl. No.: 646,171

[22] Filed: Aug. 30, 1984

[51] Int. Cl.$^4$ .......................... C12Q 1/70; C12Q 1/68; C08G 77/04
[52] U.S. Cl. ............................................. 435/5; 435/6; 435/29; 435/35; 435/39; 436/501; 436/508; 436/63; 436/94; 536/27; 536/28; 536/29; 935/77; 935/78; 935/81
[58] Field of Search ...................... 435/6, 5, 29, 35, 39; 436/501, 508, 63, 94; 536/27, 28, 29; 935/77, 78, 81

[56] References Cited

U.S. PATENT DOCUMENTS 4,486,539 12/1984 Ranki et al. ......................... 436/504

OTHER PUBLICATIONS

Martinell et al., PNAS, vol. 78, No. 8, pp. 5056–5060, 1981.

*Primary Examiner*—Christine M. Nucker
*Attorney, Agent, or Firm*—Charles J. Herron

[57] ABSTRACT

The present invention relates to a wide range of genetic analyses using the technique of nucleic acid hybridization. These genetic analyses include, for example, the diagnosis of infections by foreign microbes and the detection of specific genetic traits and abnormalities. More specifically, the present invention is related to the detection of the presence of a polynucleotide sequence of interest.

22 Claims, No Drawings

COMPOSITION AND METHOD FOR THE DETECTION OF THE PRESENCE OF A POLYNUCLEOTIDE SEQUENCE OF INTEREST

FIELD OF THE INVENTION

The present invention relates to a wide range of genetic analyses using the technique of nucleic acid hybridization. These genetic analyses include, for example, the diagnosis of infections by foreign microbes and the detection of specific genetic traits and abnormalities. More specifically, the present invention is related to the detection of the presence of a polynucleotide sequence of interest.

BACKGROUND OF THE INVENTION

A general method for the detection of a polynucleotide sequence of interest in a sample comprises:
 (a) rendering at least a portion of said polynucleotide sequence of interest in single stranded form;
 (b) providing a composition which comprises a first polynucleotide sequence which is substantially complementary and capable of hybridizing to said polynucleotide sequence of interest and which is labeled with a detectable marker;
 (c) rendering at least a portion of said composition in substantially single stranded form;
 (d) contacting said polynucleotide sequence of interest with said composition under conditions to permit hybridization; and
 (e) detecting said polynucleotide sequence of interest by means of said detectable marker.

This method is often not useful when: (1) said composition further comprises a second polynucleotide sequence which, either in the same molecule or a separate molecule, is not substantially complementary to said polynucleotide sequence of interest and which is labeled with said detectable marker; and (2) said polynucleotide sequence of interest is potentially contained in a sample that comprises polynucleotide sequences not of interest. When both conditions (1) and (2) are present, any signal detection is ambiguous as to whether said polynucleotide sequence of interest is detected or some polynucleotide sequences not of interest but hybridizable to said labeled second polynucleotide sequence are detected.

As an example, condition (1) presents itself quite naturally when said first polynucleotide sequence is produced by recombinant nucleic acid technology. Recombinant nucleic acid technology allows economic large scale production of said first polynucleotide sequence concomitant with a second polynucleotide sequence which is not substantially complementary to the polynucleotide sequence of interest, the vector sequence in this instance, on the same molecule, i.e. the recombinant molecule. Often, it is easier or more economical to label the entire recombinant molecule than to label exclusively said first polynucleotide sequence. However, this also produces a labeled second polynucleotide sequence, i.e. the vector sequence in this instance, which is not substantially complementary to said polynucleotide of interest.

As another example, condition (1) presents itself when said first polynucleotide sequence is inserted, along with a second polynucleotide sequence not substantially complementary to the polynucleotide sequence of interest, into a vector to form a single recombinant molecule. This is due to the fact that it is difficult or inconvenient to separate the first polynucleotide sequence from the second polynucleotide sequence or that the boundary between said first polynucleotide sequence and said second polynucleotide sequence is not known.

Thus, in either of the two above examples, when the method for the detection of the polynucleotide sequence of interest is carried out, the labeled second polynucleotide sequence is capable of hybridizing to a complementary polynucleotide sequence that may be contained in the sample, i.e. condition (2) is present. This can generate a false po itive result.

OBJECTS OF THE INVENTION

It is the object of the present invention to provide a composition comprising polynucleotide sequences and a method to use the same, which is effective in (1) detecting the presence or absence of a specific polynucleotide sequence of interest in a sample and (2) discriminating between the presence of said polynucleotide sequence of interest from the presence of polynucleotide sequences not of interest which may be contained in the sample.

SUMMARY OF THE INVENTION

The present invention provides a composition for detecting a polynucleotide sequence of interest in a sample which may contain polynucleotide sequences not of interest, which comprises:
 (a) a first polynucleotide sequence wherein said first polynucleotide sequence is substantially complementary to and capable of hybridizing to said polynucleotide sequence of interest and is labeled with a first detectable marker;
 (b) a second polynucleotide sequence wherein said second polynucleotide sequence is not substantially complementary to or substantially identical to said first polynucleotide sequence of interest and is labeled with said first detectable marker;
 (c) a third polynucleotide sequence wherein said third polynucleotide sequence is substantially complementary to or identical to said second polynucleotide sequence and is either unlabeled or is labeled with a second detectable marker.

The present invention further provides a method, for the detection of a polynucleotide sequence of interest in the potential or actual presence of polynucleotide sequences not of interest in a sample to be examined, which comprises:
 (a) providing a composition which comprises:
  1. a first polynucleotide sequence wherein said first polynucleotide sequence is substantially complementary to and capable of hybridizing to said polynucleotide sequence of interest and is labeled with a first detectable marker;
  2. a second polynucleotide sequence wherein said second polynucleotide sequence is not substantially complementary to or substantially identical to said first polynucleotide sequence of interest and is labeled with said first detectable marker; and
  3. a third polynucleotide sequence wherein said third polynucleotide sequence is substantially complementary to or identical to said second polynucleotide sequence and is either unlabeled or is labeled with a second detectable marker;
 (b) rendering at least a portion of, but preferably, substantially all of said polynucleotide sequence of interest and said polynucleotide sequences not of interest in said sample to be examined in single stranded form;

(c) rendering at least a portion of, but preferably, substantially all of said composition in single stranded form;

(d) contacting said polynucleotide sequence of interest and said polynucleotide sequences not of interest in said sample to be examined with said composition under conditions to permit hybridization; and (e) detecting said polynucleotide sequence of interest by means of said first detectable marker.

DETAILED DESCRIPTION OF THE INVENTION

The present invention is related to the detection of a polynucleotide sequence of interest. Preferably, the present invention is related to the detection of a polynucleotide sequence of interest in a diagnostic sample.

The polynucleotide sequence of interest can be any polynucleotide sequence present naturally in a sample or added to the sample. It can be in a material in or derived from a cellular system. It can be a subcellular component as virus or viroid or virus like particle. It can be a deoxyribonucleic acid sequence or a ribonucleic acid sequence. It can be single stranded or double stranded. It can be derived from a pathogen. It can be a sequence of a prokaryote, such as *Neisseria meningitidis* or *Neisseria gonorrhoea;* a eukaryote, such as human, or a virus such as herpes simplex virus I or herpes simplex virus II, or an extra chromosomal genetic element such as a B-lactamase specifying plasmid. The polynucleotide sequence of interest can be derived from all or any part of the genome.

COMPOSITION OF POLYNUCLEOTIDE SEQUENCES

The present invention is related to compositions of polynucleotide sequences that are useful in nucleic acid hybridizations. The compositions comprise a first polynucleotide sequence which is substantially complementary to and capable of hybridizing to a specific polynucleotide sequence of interest and which is labeled with a first detectable marker; a second polynucleotide sequence that is not substantially complementary to or substantially identical to said polynucleotide sequence of interest and that is labeled with said first detectable marker; and a third polynucleotide sequence that is substantially complementary to or substantially identical to said second polynucleotide sequence and that is unlabeled or labeled with a second detectable marker.

The first and second polynucleotide sequences can be present as separate molecules or can be covalently linked. The third polynucleotide sequence is present as a separate molecule.

The first, second and third polynucleotide sequences of the compositions of the present invention can be deoxyribonucleic acid or ribonucleic acid sequences and can be either single-stranded or double-stranded molecules. The polynucleotide sequences can be produced or obtained by any method known to those of ordinary skill in the art, e.g., synthetic production methods or enzymatic production methods, both in vitro and in vivo.

When the method of the invention is carried out, the presence of the third polynucleotide sequence in the compositions of the invention serves to block the hybridization of the second polynucleotide sequence to any polynucleotide sequences not of interest in the sample being examined, which nevertheless are substantially complementary to said second polynucleotide sequence. This blocking action limits the liklihood that the second polynucleotide sequence will generate a false positive result.

THE SECOND POLYNUCLEOTIDE SEQUENCE AS A VECTOR SEQUENCE

In one embodiment of the invention, the first polynucleotide sequence, that is substantially complementary to and capable of hybridizing to the polynucleotide sequence of interest, is cloned into a vector by standard recombinant nucleic acid technology to form a recombinant molecule.

Thus, the recombinant molecule comprises the first polynucleotide sequence and the second polynucleotide sequence, i.e. the vector in this embodiment of the invention.

The vector can be a plasmid, a cosmid, a bacterial virus or an animal virus. The vector can be ribonucleic acid or deoxyribonucleic acid. The vector can be single stranded or double stranded.

The first polynucleotide sequence, which is part of the recombinant molecule, can be produced economically in large quantities inside hosts, for example, *Escherichia coli* by fermentation. The recombinant molecule can be purified by standard methods.

For detection of the polynucleotide sequence of interest in a sample to be examined, it is desirable to label the first polynucleotide sequence present in the recombinant molecule with a first detectable marker. This can be done in more than one way.

In one method, the first polynucleotide sequence is largely separated from the vector by, for example, cutting the recombinant molecule with a restriction enzyme followed by agarose gel electrophoresis, extracted and labeled. Thus, substantially only the first polynucleotide sequence and not the vector is labeled.

In a second and more economical method the entire recombinant molecule is labeled. This method can be carried out by, for example, nick translation using DNAse I and DNA Polymerase I in the presence of labeled nucleoside triphosphates. (Rigby, P. W. et. al., J. Mol. Biol. 113:237 (1977)). This results in the recombinant molecule, i.e. the first and second polynucleotide sequences, being uniformly labeled.

The second method avoids numerous drawbacks incurred by the first method. At best, the first method is extremely tedious; each step is very time consuming, especially the step of gel electrophoresis. Often the step of gel electrophoresis needs to be repeated to insure purity of the separation of the first polynucleotide sequence. Even so, the first polynucleotide sequence may still be contaminated by trace amounts of the second polynucleotide sequence, i.e. the vector sequence. In such a case, the present invention provides a benefit. Furthermore, the inherent properties of the recombinant molecules may be such that the first and second polynucleotide sequences can not be easily separated. For example, if the first polynucleotide sequence were of the same or similar size as the second polynucleotide sequence, then the separation of such two polynucleotide sequences may not be feasible.

If the method of choice for labeling the first polynucleotide sequence causes the second polynucleotide sequence to be labeled also, and if polynucleotide sequences complementary to the second polynucleotide sequence are contained in the sample being examined, the interpretation of results of analysis based on the detection of labeled and hybridized polynucleotide sequences becomes problematic. The second polynucleotide sequence is capable of generating a false positive result.

In this embodiment of the invention, wherein the entire recombinant molecule is labeled, the compositions of the invention comprise a third polynucleotide sequence. The third polynucleotide sequence is either unlabeled or labeled with a second detectable marker and is substantially complementary to or substantially identical to the second polynucleotide sequence.

The presence of the third polynucleotide sequence in the compositions of the invention serves to block the hybridization of the second polynucleotide sequence to any polynucleotide sequences not of interest in the sample being examined, which nevertheless are substantially complementary to said second polynucleotide sequence. It is believed that this blocking action is achieved in either or both of two ways.

First, the third polynucleotide sequence, being substantially complementary to said second polynucleotide sequence, can hybridize with the second polynucleotide sequence if said second and third polynucleotide sequences are rendered single stranded and allowed to contact under conditions that permit hybridization. Second, the third polynucleotide sequence, being substantially identical to the second polynucleotide sequence, can hybridize to any polynucleotide sequences not of interest but complementary to the second polynucleotide sequence and present in the sample being examined. It is believed that either of these blocking actions inhibit the liklihood of the generation of a false positive result.

THE SECOND POLYNUCLEOTIDE SEQUENCE AS A SEQUENCE CONTIGUOUS TO BUT DISTINCT FROM THE FIRST POLYNUCLEOTIDE SEQUENCE IN THE CHROMOSOME

In another embodiment of the invention, the first polynucleotide sequence, which is substantially complementary to and capable of hybridizing to the polynucleotide sequence of interest, is covalently linked in the chromosome to the second polynucleotide sequence that is not substantially complementary or substantially identical to the polynucleotide sequence of interest, but which can potentially be substantially complementary to polynucleotide sequences not of interest in the sample being examined. The first polynucleotide sequence and the second polynucleotide sequence can have a single boundary or multiple boundaries. The boundaries can be known or unknown. In some instances, it is difficult at best and generally impossible to isolate said first polynucleotide sequence from said second polynucleotide sequence. Consequently, it is preferable to label both the first and second polynucleotide sequences.

A specific example of this embodiment of the present invention is wherein the first polynucleotide sequence is a polynucleotide sequence specific for genetic material of Neisseria gonorrhoea. A polynucleotide sequence is said to be specific for polynucleotide sequence A if and only if said polynucleotide sequence is capable of hybridizing exclusively to polynucleotide sequence A. It is known that Neisseria gonorrhoea and Neisseria meningitidis share significant nucleic acid homology; in excess of 80% of the polynucleotide sequence of the Neisseria gonorrhoea genome is substantially complementary or substantially identical to the polynucleotide sequence of the Neisseria meningitidis genome (Kingsbury, D. T. J. Bact. (1967) 94, p 870–874). In this example, a polynucleotide fragment, derived from Neisseria gonorrhoea deoxyribonucleic acid, comprising a first polynucleotide sequence specific for N. gonorrhoea and a second polynucleotide sequence specific for the species N. gonorrhoea and N. meningitidis, is cloned into a vector to form a recombinant DNA molecule. The first and second polynucleotide sequences are purified from the vector and are both labeled with a first detectable marker. The composition of the invention provides, in addition to such labeled first and second polynucleotide sequences, a third polynucleotide sequence which is not labeled with said first detectable marker and which is substantially complementary to or substantially identical to said second polynucleotide sequence. The third polynucleotide sequence, when present in suitable amounts, will effectively prevent said labeled second polynucleotide sequence from hybridizing to the polynucleotide sequence not of interest, i.e. the sample may comprise N. meningitidis DNA. Thus, a false positive signal will not be generated.

The third polynucleotide sequence can be provided in one of several ways. For example, a recombinant molecule consisting of a vector and an inserted polynucleotide sequence, isolated from N. meningitidis, which comprises a polynucleotide sequence or sequences which are substantially complementary or substantially identical to said second polynucleotide sequence can be added to the composition. Preferably, total genomic N. meningitidis DNA, which comprises the third polynucleotide sequence, can be added to the composition.

In another specific example of this embodiment of the present invention, the specific polynucleotide sequence of interest is a sequence specific for herpes simplex virus I. The first polynucleotide sequence is specific for herpes simplex virus I DNA. The second polynucleotide sequence which is labeled is a sequence specific for herpes simplex virus I DNA and herpes simplex virus II DNA. The third polynucleotide sequence which is not labeled is a sequence substantially complementary to or substantially identical to said second polynucleotide sequence, i.e. that portion of herpes simplex virus II DNA that is specific for herpes simplex virus I DNA and herpes simplex virus II DNA, if known. Said third polynucleotide sequence can be provided, for example, by including in the composition, total genomic herpes simplex virus II DNA. This composition permits the detection of the specific polynucleotide sequence of interest, i.e. herpes simplex virus I DNA and inhibits the liklihood of the second polynucleotide sequence from detecting herpes simplex virus II DNA.

Further non-limiting examples of this embodiment of the present invention are listed in Table I below:

TABLE I

| Specificity of 1st polynucleotide Sequence | Specificity of 2nd polynucleotide Sequence | Specificity of 3rd polynucleotide Sequence |
|---|---|---|
| Brucella abortus | Brucella abortus and B. melitenis | Brucella abortus and B. melitenis |
| Bordetella pertussis | B. pertussis and B. parapertussis | B. pertussis and B. parapertussis |
| Shigella dysenteria | Shigella dysenteria and E. coli | Shigella dysenteria and E. coli |
| Haemophilus influenzae | H. influenzae H. parainfluenzae | H. influenzae H. parainfluenzae |
| Mycobacterium tuberculosis | M. tuberculosis and M. bovis | M. tuberculosis and M. bovis |

TABLE I-continued

| Specificity of 1st polynucleotide Sequence | Specificity of 2nd polynucleotide Sequence | Specificity of 3rd polynucleotide Sequence |
| --- | --- | --- |
| Pseudomonas pseudomallei | Ps. psuedomallei and Ps. mallei | Ps. psuedomallei and Ps. mallei |
| Salmonella typhi | S. typhi and S. typhimurium | S. typhi and S. typhimurium |
| Salmonella typhimurium | S. typhimurium and S. choleraesuis | S. typhimurium and S. choleraesuis |

THE SECOND POLYNUCLEOTIDE SEQUENCE AS A HOST SEQUENCE

In a third embodiment of the invention, the first polynucleotide sequence, i.e. the polynucleotide sequence that is substantially complementary to and capable of hybridizing to the polynucleotide sequence of interest, is produced inside hosts as an extrachromosomal polynucleotide sequence. The second polynucleotide sequence is the host polynucleotide sequence.

The first polynucleotide sequence can be substantially purified by standard methods. However, it may be contaminated with a trace amount of the second polynucleotide sequence, i.e. the host polynucleotide sequence. Thus, when the first polynucleotide sequence is labeled with a first detectable marker, a trace amount of the host polynucleotide sequence is also labeled. If the sample to be examined contains polynucleotide sequences complementary to the second polynucleotide sequence, i.e. the host polynucleotide sequence, a false positive result can be generated. To prevent this undersirable result, the composition of the invention provides a third polynucleotide sequence which, in this embodiment, is the host sequence that is not labeled with said first detectable marker.

A specific example of this embodiment of the present invention is wherein the first polynucleotide sequence is an enteroinvasive plasmid, which is grown in $E.$ $coli$ hosts. The sample to be examined is derived from the stool of a human patient. This sample is then expected to contain $E.$ $coli$ polynucleotide sequence. If the labeled first polynucleotide sequence is contaminated even with a small amount of labeled second polynucleotide sequence, i.e. $E.$ $coli$ polynucleotide sequence, a false positive result can be generated. However, inclusion of a third polynucleotide sequence, i.e. unlabeled $E.$ $coli$ polynucleotide sequence, will inhibit the likelihood of this undesirable result.

Of course, in certain embodiments of the present invention, the three embodiments discussed above, namely, the second polynucleotide sequence as a vector sequence, the second polynucleotide sequence as a sequence chromosomally linked to the first polynucleotide sequence and the second polynucleotide sequence as a host polynucleotide sequence can be combined. The third polynucleotide sequence, which is not labeled with the first detectable marker, can comprise a sequence which is substantially complementary or substantially identical to said vector sequence and said sequence which is chromosomally linked to said first polynucleotide sequence, and a polynucleotide host sequence.

Also, in certain embodiments of the present invention only two of the three embodiments discussed are combined.

PREFERRED MOLECULAR FORM OF THIRD POLYNUCLEOTIDE SEQUENCE

Experiments were performed to determine the optimal size distribution of the third polynucleotide sequence in the compositions provided by the present invention. It is believed that the third polynucleotide sequence fragments can be essentially any length, provided that the fragments are long enough to form a stable hybrid. However, a preferred embodiment of the invention is wherein the third polynucleotide sequence fragments are from about 50 to about 250 nucleotides in length. These short fragments are preferably produced by controlled digestion with DNAse I. Alternatively, sonication or digestion with other suitable nucleases can be used.

Experiments were also performed to determine the appropriate amount of third polynucleotide sequence in the composition of the present invention. It was found that the higher the amount of third polynucleotide sequence in the composition, the more effective said composition was in blocking the signal generated by the first detectable marker on the second polynucleotide sequence. The amount of third polynucleotide sequence to be utilized is dependent upon how the method of the invention is carried out, as discussed hereinbelow.

DETECTABLE MARKERS AND DETECTION

A labeled polynucleotide sequence in this invention means a polynucleotide sequence which is labeled with a detectable marker. Any detectable markers now in use in the art of nucleic acid hybridization or to be developed in the future can be used. The choice of detectable markers, is not critical to the present invention. Suitable detectable markers include radioactive nuclides; chemical markers including biotinated moieties, antigens, sugars, fluors and phosphors, enzymes, apoenzymes and cofactors, ligands, allosteric effectors, ferritin, dyes, microspheres.

A first detectable marker is said to differ from a second detectable marker in the context of the present invention whenever an effective method exists and is used, that discriminates said first detectable marker from said second detectable marker. For example, $^3H$ and $^{32}P$ are both radioactive markers. They are different detectable markers in the context of programmed scintillation counting that discriminate higher energy disintegrations of $^{32}P$ from low energy disintegration from $^3H$. They are not different detectable markers if the scintillation counting does not discriminate the energy of disintegration.

Another example is provided by the following pair of labeled polynucleotide sequences: A is a polynucleotide sequence labeled with biotinylated nucleotides; B is is polynucleotide sequence labeled at the 3'-terminus with poly T. A is detected by an avidin-horseradish peroxidase complex which generates a color in the presence of a suitable chromogen substrate. This method is disclosed in co-pending, co-assigned U.S. patent application Ser. Nos. 574,632, filed Jan. 26, 1984 and 461,469, filed Jan. 27, 1983, the disclosures of which are incorporated herein by reference. B is detected indirectly through a biotinylated-poly A polynucleotide bridge. The biotin contained in said poly A polynucleotide is detected by said avidin-horseradish peroxidase complex in the presence of said chromogen substrate. This method is disclosed in co-pending, co-assigned U.S. patent application Ser. No. 491,929, filed May 5, 1983.

The detection of A and B, if desired, can be separated. If, in fact, the detection of A and B is separated, then A and B are different detectable markers. If, in fact, the detection of A and B is not separated, then A and B are not different detectable markers.

METHODS OF USING THE POLYNUCLEOTIDE COMPOSITIONS OF THE PRESENT INVENTION

The present invention also relates to methods of using the compositions of the present invention. The compositions can be used in all nucleic acid hybridization procedures. These procedures include, but are not limited to two phase hybridization and one phase hybridization. Examples of two phase hybridization are hybridization in situ and hybridization to polynucleotide sequences immobilized on a transparent and nontransparent surface. An example of one phase hybridization is hybridization to polynucleotide sequences in solution. The choice of a particular procedure is not critical to the present invention.

The genetic material of the sample to be examined is prepared as called for in the particular procedure being used, which is or will be known to a person of ordinary skill in the art. These procedures result in at least a portion of the genetic material of the sample being in single stranded form, but preferably substantially all of the genetic material of the sample is in single stranded form.

At least a portion of the polynucleotide sequences of the compositions of the invention are rendered in single stranded form. However, it is highly preferred that said polynucleotide sequences be rendered in substantially single stranded form because polynucleotide sequences in duplex form generally do not participate in hybridization. Each component, namely, the first polynucleotide sequence, the second polynucleotide sequence and the third polynucleotide sequence can be rendered in substantially single stranded form singly or together in any combination. The polynucleotide sequences in said composition, thus rendered in single stranded form, are utilized to contact the prepared genetic material of the sample to be examined, which has been rendered in single stranded form, under conditions that permit hybridization. It is highly preferred that the third polynucleotide sequence be allowed to contact the prepared sample prior to, or at substantially the same time as the second polynucleotide sequence. Otherwise, given time during which the third polynucleotide sequence is absent, the second polynucleotide sequence can hybridize to complementary polynucleotide sequences not of interest, if present, in the sample being examined. This would defeat the purpose of including the third polynucleotide sequence in the composition and generate a false positive result upon detection of the first detectable marker. Within this preferred condition, there are three preferred embodiments for practicing the method of the invention.

In the first preferred embodiment of the method of the invention the first, second and third polynucleotide sequences of the composition are contacted with the sample to be examined at about the same time. In this embodiment it is preferred that the third polynucleotide sequence is present in the composition in an amount by weight from about 100 to about 1000 fold greater than the amount of the second polynucleotide sequence in the composition. Amounts greater than about 1000 fold blocked essentially no more of the second polynucleotide sequence. However, if the sample contains a greater amount of polynucleotide sequence not of interest, but capable of hybridizing to the second polynucleotide sequence than the amount of second polynucleotide sequence in the composition, then the third polynucleotide sequence should be present in an amount by weight from about 100 to about 1000 fold greater than the amount of the polynucleotide sequence not of interest but capable of hybridizing to the second polynucleotide sequence. As a practical matter, the latter situation is very rarely of concern.

In the second preferred embodiment of the method of the invention, the first, second and third polynucleotide sequences are allowed to contact each other in solution and hybridize for a substantial amount of time so that the hybridization of the second polynucleotide sequence is substantially complete and that the hybridization of the first polynucleotide sequence is not. In this embodiment it is preferred that the third polynucleotide sequence be present in the composition in an amount by weight from about 100 to about 1000 fold greater than the amount of the second polynucleotide sequence in the composition. This excess of the third polynucleotide sequence accelerates the hybridization of the second polynucleotide sequence without accelerating the renaturation of the first polynucleotide sequence. With respect to the extra time required and the extra step necessary to obtain a result, this embodiment is less preferred. But this embodiment of the invention is more preferred if the sample to be examined contains sigificant amounts of polynucleotide sequences not of interest but capable of hybridizing to the second polynucleotide sequence. This is because the second polynucleotide sequence in the composition has already hybridized substantially to completion and can not hybridize to any polynucleotide sequence in the sample.

In the third preferred embodiment of the method of the invention, the third polynucleotide sequence of the composition is allowed to contact with and hybridize substantially to completion with the genetic material in the sample to be examined prior to the contacting of the second polynucleotide sequence with the genetic material in the sample. In this embodiment it is preferred that the third polynucleotide sequence be present in the composition in an amount by weight from about 10 fold to about 100 fold greater than the amount of the polynucleotide sequence not of interest but capable of hybridizing to the second polynucleotide sequence in the composition. This amount is generally sufficient to hybridize with all polynucleotide sequences not of interest but capable of hybridizing to the second polynucleotide sequence in the composition. This embodiment is not preferred with respect to the extra time required and the extra step necessary to obtain a result. But it is preferred with respect to the quantity of the third polynucleotide sequence required for the composition when the sample to be examined contains significant amounts of polynucleotide sequence not of interest but capable of hybridizing to the second polynucleotide sequence.

At the end of the hybridization reaction, the stable hybrid genetic material formed is detected by means of the first detectable marker.

In certain embodiments of this invention, after the hybridization reaction is over, the detection step requires a separation step which separates that part of the composition which has hybridized to the sample being examined from that part which has not. Such separation can be carried out by a wash step. For example, the sample to be examined is immobilized on a nitrocellulose filter. Biotinylated nucleotides are used to label the first and second polynucleotide sequences. At the end of the hybridization reaction, the nitrocellulose filter is washed so that unhybridized sequences in the composition are removed. The biotinylated nucleotides contained in the molecules which are bound to the immobilized target are then detected by any suitable means.

In certain embodiments of this invention, after hybridization is over, a separation step is not necessary in the detection process. For example, this is the case when the detectable marker used is an asymmetric chemiluminescent emitter/absorber system. In this embodiment, a signal is generated only if the labeled polynucleotide sequences in the composition have hybridized with substantially complementary sequences in the sample being examined. This method of detection is disclosed in European Patent Publication No. 0 070 685, published Jan. 26, 1983. Another example utilizes a agglutinable microsphere as the detectable marker. This method is disclosed in co-pending, co-assigned U.S. patent application Ser. No. 605,022 filed Apr. 27, 1984.

MULTIPLE DETECTION

The third polynucleotide sequence of the composition can, if so desired, be labeled with a second detectable marker. It is then possible to detect any third polynucleotide sequence that hybridizes with the genetic material in the sample, and, by inference, the presence of a polynucleotide sequence not of interest but capable of hybridizing to the second polynucleotide sequence of the composition. Such detection can give a benefit if the quantity of said polynucleotide sequence not of interest in the sample is large, as indicated by the signal generated by the second detectable marker, it may become necessary to re-assess the significance of a positive result, if any, from the first detectable marker. This is because some fraction of the second polynucleotide sequence may have hybridized to said polynucleotide sequence not of interest in the sample and contributed to the signal from the first detectable marker.

The following examples are offered by way of illustration and not by way of limitation.

EXAMPLE I

Introduction

In this example of the invention, a model system was used to demonstrate the detection of a polynucleotide sequence of interest, a 9 kilobase DNA fragment of *Chlamydia trachomatis*, in the presence of a polynucleotide not of interest, pBR322.

Plasmids

The plasmid pCHL2 consists of a 9 kilobase BamH I fragment from *Chlamydia trachomatis* cloned into the BamH I site of the plasmid pBR322. The 9 kilobase BamH I fragment has no substantial complementarity to pBR322.

Preparation of Target Samples

Sonicated pCHL2 plasmid DNA at a concentration of 220 ug/ml in 10 mM Tris-HCl pH 7.5, 0.1 mM EDTA was denatured by the addition of NaOH to a final concentration of 0.5M. A volume of 1M Tris-HCl pH 7.5 equal to that of the alkaline DNA solution was added to neutralize the solution. 20X SSC was then added to a final concentration of 2X SSC, (1X SSC=0.15M NaCl, 0.015M Na citrate pH 7.0). An amount equivalent to 2 ug of DNA was then applied to each of 30 points on a nitrocellulose filter (previously wetted with distilled water at 65° C. and then soaked in 6X SSC) using a "minifold dot blot" apparatus. Each well was rinsed with 200 ul of 2X SSC, and the filter was then air dried and baked for 2 hours at 80° C. in vacuo. Each spot on the filter was then punched out to yield 30 small circular filters, 3/16 inch in diameter and containing 2 ug bound, denatured pCHL2 DNA. As control "targets" 30 similar filters were punched from a nitrocellulose filter to which no DNA had been applied.

Preparation of Polynucleotide Composition

A. Preparation of Labeled Polynucleotide Sequences

1. Isolation of the Chlamydia Fragment pCHL2 was digested with the restriction enzyme BamH I, and the resulting fragments separated on an 0.5% low melting temperature agarose gel. The band corresponding in size to 9.0 kb was cut from the gel, and the DNA extracted from the gel slice using sodium iodide and powdered flint glass as described by Vogelstein and Gillespie (Proc. Natl. Acad. Sci. USA 76: 615-617, 1979). An aliquot of this purified fragment was run on 0.7% agarose gel to check for contamination of the purified chlamydia fragment by the pBR322 vector. No contamination of the pure fragment was seen. However, the remaining chlamydia DNA fragment was subjected to a second round of gel electrophoresis and isolation to obviate any possibility of contamination by the pBR322 vector sequence.

2. Nick Translation of DNA Probes

To 2 ug of DNA in 10 mM Tris-HCl pH 7.4, 0.1 mM EDTA, was added 10 ul of 10X nick translation buffer (0.5M Tris-HCl pH 7.5, 0.05M $MgCl_2$, 0.1M Beta mercaptoethanol, 0.5 mg/ml bovine serum albumin) and distilled water to a total volume of 85 ul. To this was added 1 ul of DNase I (freshly diluted 5000 fold in 1X nick translation buffer from a 1 mg/ml stock solution). The reaction was incubated at 37° C. for 5 minutes and then at 68° C. for 10 minutes.

1 ul each of 100 mM dATP and dTTP was then added to the reaction mixture on ice followed by 50 mCi of either $^3$H- or $^{32}$P-dCTP and dGTP. The reaction mixture was incubated at 14° C. for 5 minutes when 2 ul of DNA polymerase I (equivalent to 20 units) was added. After 30 minutes at 14° C. the reaction was stopped by the addition of 4 ul of 0.5M EDTA, and the reaction placed on ice. Radioactively labeled DNA was separated from unincorporated nucleotides using a sephadex G50 (medium) column.

Pure chlamydia fragment DNA was nick translated with $^{32}$P labeled nucleotides to a specific activity of $2.1 \times 10^7$ cpm/ug and pBR322 was nick translated with $^3$H labeled nucleotides to a specific activity of $3 \times 10^6$ cpm/ug.

B. Preparation of Unlabeled Polynucleotide Sequence 31 ug of pBR322 in 145 ul of T. E. (10 mM Tris-HCl, 0.1 mM EDTA pH 7.5) was degraded to molecules of size varying from about 25 to about 125 base pairs using DNase I digestion. DNase I was stored at −20° C. as a 1 mg/ml solution in 0.01N HCl, 50% glycerol and diluted immediately before use in T. E. Digestion was carried out in a total volume of 200 ul containing: 50 mM Tris pH 7.5, 1 mM $MnCl_2$, 100 ug/ml bovine serum albumin and 100 ng of DNase I at 37° C. for 10 minutes. The reaction was stopped by addition of 20 ul of 0.5M EDTA on ice. The products of digestion were analyzed on a 4% agarose gel using HinF I digested pBR322 as molecular weight markers.

Hybridizations with Sample DNA or Control Filters

Nitrocellulose filters with sample DNA or control filters were pre-hybridized in batches of 30 discs in 250 ml beakers containing 50 ml of prehybridization solution at 65° C. Prehybridization was for 10 minutes in 3X SSC, 60 minutes in 3X SSC, 5X Denhardt's, (5X Denhardt's=0.1% Ficoll, 0.1% Polyvinyl pyrolidone, 0.1% bovine serum albumin) and 2 hours in 3X SSC, 5X Denhardt's 0.1% SDS (Na dodecyl sulfate) and 100 ug/ml sonicated calf thymus DNA which was boiled for 5-7 minutes immediately before addition.

Hybridizations were carried out in 1.5 ml Eppendorf tubes in a total volume of 500 ul and contained 3X SSC, 5X Denhardt's, 0.1% SDS and 100 ug/ml calf thymus DNA. Tubes 1 to 16 received a nitrocellulose filter disc with pCHL2 DNA. Tubes 17 to 32 received control discs with no target sequence. Unlabeled, DNase I digested pBR322 DNA was boiled for 5 to 7 minutes and then placed on ice. It was added to tubes 1 to 16 and 17 to 32 in amounts by weight representing 0, 5, 10, 20, 30, 40, 50, 60, 70, 80, 90, 100, 150, 200, 500 and 1000 fold excess over the amount of $^3$H labeled pBR322 DNA. $1.25 \times 10^5$ cpm of boiled $^3$H labeled DNA was added to each of the hybridizations, representing the ng of DNA contained in 53 ul. The same number of cpm of $^{32}$P labeled chlamydia DNA was added in a volume of 6.0 ul. Hybridizations were allowed to proceed at 65° C. with skaking for 16 hours.

Washing of the Filters

Each filter was washed quickly, 3 times with 2X SSC, 0.1% SDS at 65° C. and then washed 4 times for 30 minutes each wash at 65° C. in 2X SSC, 0.1% SDS. Filters were then dried under an infrared lamp, added to scintillation vials and counted using an "Omnifluoer" scintillation fluid. Vials were counted in a Beckman LS6800 scintillation counter programmed to discriminate $^3$H and $^{32}$P counts. One energy spectrum channel of the scintillation counter was set to detect low energy $^3$H disintegrations in the range of 0 to 300.

A second channel was set to direct high energy $^{32}$P disintegrations in the range of 500 to 1000. Under these conditions, spillover into the first channel by $^{32}$P counts was 1.65% that of the second channel counts and spillover into the second channel by $^3$H counts was less than 0.1% that of the first channel.

| Ratio of Unlabeled DNAsed pBR322 DNA to $^3$H Labeled pBR322 DNA | $^{32}$P counts | % | $^3$H counts | % |
|---|---|---|---|---|
| RESULTS | | | | |
| 0 | 30,178 | 105 | 12,735 | 100 |
| 5 | 28,742 | 100 | 8,402 | 66 |
| 10 | 25,003 | 87 | 6,565 | 52 |
| 20 | 29,501 | 103 | 4,737 | 37 |
| 30 | 25,466 | 89 | 3,564 | 28 |
| 40 | 31,659 | 110 | 3,228 | 25 |
| 50 | 30,875 | 108 | 2,495 | 20 |
| 60 | 31,301 | 109 | 2,509 | 20 |
| 70 | 33,752 | 117 | 2,578 | 20 |
| 80 | 28,571 | 100 | 2,142 | 17 |
| 90 | 29,413 | 102 | 1,733 | 14 |
| 100 | 27,937 | 97 | 1,568 | 12 |
| 150 | 23,132 | 81 | 1,030 | 8 |
| 200 | 25,607 | 89 | 915 | 7 |
| 500 | 30,718 | 107 | 506 | 4 |
| 1000 | 27,580 | 96 | 267 | 2 |

Background counts from the 16 control filters ranged from 5.90 cpm to 13.60 cpm.

At a thousand fold excess unlabeled, DNAsed pBR322 DNA over $^3$H labeled pBR322 DNA, 98% of the $^3$H signal can be suppressed. At the same time, the results indicate that the signal from the $^{32}$P labeled *Chlamydia trachomatis* DNA bound to its complementary sequence on the filter as unaffected.

EXAMPLE II

In the example of the invention, it was demonstrated that any amount of unlabeled pBR322 that has been digested by DNase I to a size varying from about 25 to about 125 nucleotides in length was more effective than the same amount of unlabeled, full length linear pBR322 in blocking the hybridization of labeled pBR322 DNA to its complementary sequence target.

Plasmids

The same plasmids cited in Example I, namely, pCHL2, pBR322 were used.

Preparation of Target Samples

The 9 kilobase DNA fragment from *Chlamydia trachomatis* was purified as described in Example I. Intact, supercoiled pBR322 DNA was disrupted by brief sonication. Separately, each DNA was treated sequentially with NaOH, Tris-HCl pH 7.5 and 20X SSC as described in Example I. 200 ng samples of pBR322 DNA or *Chlamydia trachomatis* DNA were applied on nitrocellulose filters as described in Example I. The filters were then dried and baked for 2 hours at 80° C. in vacuo. Each spot on the filter was then cut out to yield 3/16 inch diameter circular filters containing *Chlamydia trachomatis* DNA or 3/16 inch × 3/16 inch square filters containing pBR322 DNA or control filters of 3/16 inch diameter containing no DNA.

Preparation of Labeled Polynucleotide Sequences

The entire plasmid pCHL2, containing the vector sequence pBR322 and *Chlamydia trachomatis* sequence, was nick translated as previously described in Example I using $^{32}$P labeled deoxynucleotides to a specific activity of $1.5 \times 10^7$ cpm per ug.

Preparation of Unlabeled pBR322 DNA

1. Plasmid pBR322 DNA was treated with DNase I in the presence of Mn++ ions as described in Example I to produce molecules with a median size of approximately 50 base pairs.
2. Plasmid pBR322 DNA was linearized by digestion with BamH I.

Hybridization

Filters, either discs containing chlamydia fragment DNA, squares in containing pBR322 DNA or control discs with no target DNA, were pre-hybridized in batches as described previously in Example I. Hybridizations were carried out in a volume of 500 ul in 1.5 ml Eppendorf tubes as in Example I. 8.8 ng of nick translated pCHL2 DNA ($1.25 \times 10^5$ cpm) was added to each hybridization. The first 26 hybridizations each contained one circular and one square filter. In addition, unlabeled, DNased pBR322 DNA or BamH I digested pBR322 DNA was added in varying amounts and corresponding to a 0, 5, 10, 20, 30, 40, 50, 60, 70, 80, 90, 100, 150, 200, 500 or 1000 fold excess by weight over the labeled probe. 26 control hybridizations were set up in the same way except that one nitrocellulose filter which contained no target DNA sequence was added to each hybridization. Hybridization and washing conditions were as previously described in Example I.

Filters were dried and each filter counted separately in a scintillation counter.

hybridization reaction, corresponding to 0.47 ug of probe DNA.

Preparation of Unlabeled Polynucleotide Sequences

1. Since the radioactively labeled polynucleotide sequences pAL1 used in this experiment contained the vector plasmid pBR322, unlabeled pBR322, was used in a 1000 fold excess by weight in the hybridization reactions to block any unwanted signal from this component of the labeled polynucleotide sequence. The unlabeled pBR322 DNA was prepared by sonication of plasmid DNA to produce linear fragments of a median size of approximately 300 base pairs.

RESULTS

| Gravimetric ratio of unlabeled pBR322 DNA/labeled pCHL2 DNA | Using Unlabeled, DNAsed pBR322 DNA | | Using BamH I digested full length, unlabeled pBR322 DNA | |
|---|---|---|---|---|
| | cpm Bound to Chlamydia target | cpm Bound to pBR322 target | cpm Bound to Chlamydia target | cpm Bound to pBR322 DNA |
| 0 | 13,211 | 6,696 | 14,471 | 6,824 |
| 5 | 12,983 | 4,318 | 13,066 | 5,075 |
| 10 | 15,442 | 3,602 | 12,679 | 4,328 |
| 20 | 12,441 | 2,594 | 12,942 | 2,997 |
| 30 | 12,206 | 2,066 | — | — |
| 40 | 10,630 | 1,602 | — | — |
| 50 | 13,940 | 1,356 | 12,212 | 1,747 |
| 60 | 13,392 | 1,451 | — | — |
| 70 | 14,877 | 1,234 | — | — |
| 80 | 12,635 | 1,197 | — | — |
| 90 | 13,108 | 1,115 | — | — |
| 100 | 14,734 | 1,016 | 12,850 | 1,953 |
| 150 | 14,247 | 764 | 10,846 | 2,072 |
| 200 | 15,659 | 649 | 11,909 | 1,849 |
| 500 | 12,509 | 324 | 12,078 | 1,577 |
| 1000 | 13,261 | 200 | 10,620 | 1,056 |

EXAMPLE III

This example illustrates how a recombinant plasmid, consisting of a DNA fragment from *Neisseria gonorrhea* cloned into the vector pBR322, can be used to detect *N. gonorrhea* DNA even if said fragment comprises a sequence that is a substantially complementary to some sequence of *Neisseria meningitidis*.

Plasmids pAL1 consists of a 1.1 kb fragment of *N. gonorrhea* DNA cloned into the Pst I site of pBR322 by the homopolymer dG:dC tailing method.

Preparation of Target Samples

Chromosomal DNA from *N. gonorrhea* or *N. meningitidis* was prepared by the method of Marmur (J. Mol. Biol. 3: 208–218, (1961). 2 ug of *N. gonorrhea* DNA or 2 ug of *N. meningitidis* DNA were immobilized on each of 16 circular and square nitrocellulose filters respectively as described in Examples I and II. Control filters contain no DNA.

Preparation of labeled Polynucleotide Sequence

Plasmid pAL1 DNA was labeled by nick translation as described previously in Example I using four $^{32}$P labeled nucleotides. The specific activity of the labeled DNA was $2.7 \times 10^8$ cpm/ug. $1.25 \times 10^5$ cpm of the radioactively labeled probe were to be added to each 500 ul 2. Chromosomal DNA from a strain of *N. meningitidis*, which had been shown to cross-react with the probe pAL1 was disrupted by sonication to produce linear molecules of a median size of approximately 300 base pairs. DNA was ethanol precipitated and resuspended at a concentration of 10 mg/ml in distilled water.

Hybridization

Hybridizations were set up at 65° C. and contained 3X SSC, 5X Denhardt's, 0.1% SDS and 100 ug/ml calf thymus DNA. Tubes 1 to 16 received one circular filter with 2 ug of *N. gonorrhoeae* DNA and one square filter with .2 ug of *N. meningitidis* DNA. Tubes 17 and 32 received one control filter. Unlabeled pBR322 DNA was added at 1000 fold excess and unlabeled *N. meningitidis* DNA was added at a 0, 125, 250, 500, 103, $2 \times 10^3$, $3.9 \times 10^3$, $7.8 \times 10^3$, $1.6 \times 10^4$, $6.25 \times 10^4$, $1.25 \times 10^5$, $2.5 \times 10^5$, $5 \times 10^5$, $10^6$ and $2 \times 10^6$ fold excess over the amount of pAL1 probe DNA. DNA was boiled for 5 to 7 minutes and then placed on ice before addition to hybridization reactions. Hybridization was carried out for 16 hours at 65° C.

The filters were then rinsed 3 times with 2X SSC, 0.1% SDS at 65° C. Filters were dried under an infrared lamp and counted separately in a Beckman LS6800 scintillation counter using a standard scintillation cocktail.

RESULTS

| Relative Conc. Suppressor/probe | cpm bound to N. gonnhorea filter | % | cpm bound to N. meningitidis filter | % of Counts bound to n.g. filter at 0 suppression |
|---|---|---|---|---|
| 0 | 3,084 | 100 | 291 | 9.4 |
| 125 | 3,241 | 105 | 253 | 8.2 |
| 250 | 3,072 | 100 | 250 | 8.1 |
| 500 | 3,512 | 114 | 265 | 8.6 |
| $10^3$ | 3,429 | 111 | 228 | 7.4 |
| $2 \times 10^3$ | 2,489 | 81 | 195 | 6.3 |
| $3.9 \times 10^3$ | 2,467 | 80 | 165 | 5.4 |
| $7.8 \times 10^3$ | 2,727 | 88 | 136 | 4.4 |
| $1.6 \times 10^4$ | 2,786 | 90 | 95 | 3.1 |
| $3.13 \times 10^4$ | 2,295 | 74 | 67 | 2.2 |
| $6.25 \times 10^4$ | 2,385 | 77 | 42 | 1.4 |
| $1.25 \times 10^5$ | 2,238 | 73 | 64 | 2.1 |
| $2.5 \times 10^5$ | 2,106 | 68 | 43 | 1.4 |
| $5 \times 10^5$ | 1,195 | 39 | 26 | 0.8 |
| $10^6$ | 821 | 27 | 14 | 0.5 |
| $2 \times 10^6$ | 741 | 24 | 3 | 0.1 |

A number of important conclusions may be drawn from these results:

1. The number of counts bound to the filter containing N. meningitidis DNA was 9.4% of the counts bound to the filter containing N. gonorrhoeae DNA. Therefore, some portion of the 1.1 kb fragment of N. gonorrhoeae DNA contained in pAL1 was substantially complementary to N. meningitidis target.

2. The addition of increasing amounts of unlabeled N. meningitidis DNA in hybridization reactions suppressed hybridization of labeled pAL1 to the N. gonorrhoeae target as well as the N. meningitidis target. When unlabeled N. meningitidis DNA was added to a $2 \times 10^6$ fold excess, the hybridization of the pAL1 probe to the N. gonorrhoeae target DNA is reduced to 24% of the normal value. Under the same conditions, the hybridization of the pAL1 probe to N. meningitidis target DNA is reduced to almost undetectable levels.

3. An amount of unlabeled N. meningitidis DNA can be chosen ($3 \times 10^4$ fold excess,) at which cross-reactivity of the probe with N. meningitidis chromosomal DNA is reduced to only 2% while the probe retains 74% of its affinity for N. gonorrhea chromosomal DNA.

4. This example illustrated how this invention can be used to avoid mis-identifying N. meningitidis DNA for N. gonorrhea DNA.

What is claimed is:

1. In a composition for detecting the presence of a polynucleotide sequence of interest in a sample of polynucleotide sequences comprising:
a composition comprising at least one first and at least one second polynucleotide the improvements comprising:
(a) said first and second sequences are labeled with a first detectable marker and are either present as separate molecules from which said first polynucleotide sequence has not been isolated or are covalently linked and further characterized in that said first sequence is capable of hybridizing to said sequence of interest and said second sequence is not capable of hybridizing to said sequence of interest and is not capable of hybridizing to said first sequence; and
(b) a composition comprising at least one third polynucleotide sequence that is unlabeled or is labeled with a second detectable marker and characterized in that said third sequence is not capable of hybridizing to said first sequence and is not capable of hybridizing to said sequence of interest, and further characterized in that said third sequence is:
(i) capable of hybridizing to said second sequence, such that by hybridizing to said second sequence said third sequence blocks hybridization between said second sequence and complementary non-target sequences that may be contained in the sample and decreased the likelihood that said second sequence will generate a false positive signal upon detection of said first detectable marker; or
(b) substantially identical to said second sequence, such that by means of hybridizing to said complementary non-target sequences that may be contained in the sample said third sequence blocks hybridization between said second sequence and said complementary non-target sequences and decreases the likelihood that said second sequence will generate a false positive signal upon detection of said first detectable marker.

2. A composition as in claim 1 wherein said second polynucleotide sequence comprises a vector polynucleotide sequence.

3. A composition as in claim 1, wherein said first polynucleotide sequence is covalently linked to said second polynucleotide sequence in a chromosome.

4. A composition as in claim 3, wherein said second polynucleotide sequence further comprises a vector polynucleotide sequence.

5. A composition as in claims 3 or 4, wherein said first polynucleotide sequence is capable of hybridizing to a polynucleotide sequence selected from the group consisting of N. gonorrhoea, herpes simplex virus I, herpes simplex virus II, Brucella abortus, Bordetella pertussis, Shigella dysenteria, Haemophilus influenzae, Mycobacterium tuberculosis, Pseudomonas pseudomallei, Salmonella typhi, Salmonella typhimurium and N. meningitidis.

6. A composition as in claim 1, wherein said second polynucleotide sequence is a host polynucleotide sequence.

7. A composition as in claim 1, wherein said third polynucleotide sequence is unlabeled.

8. A composition as in claim 1, wherein said third polynucleotide sequence is present in an amount by weight from about 100 to about 1000 fold greater than said second polynucleotide sequence of said composition.

9. A composition as in claim 1, wherein said third polynucleotide sequence is from about 50 to about 250 nucleotides in length.

10. A composition as in claim 1 wherein said first and second detectable markers are selected from the group consisting of radioactive nuclides and chemical labels.

11. A composition as in claim 10, wherein said chemical label is selected from the group consisting of biotinated moieties, antigens, sugars, fluors, phosphors, enzymes, apoenzymes and cofactors, ligands, allosteric effectors, ferritin, dyes and microspheres.

12. In a method for the detection of a polynucleotide sequence of interest in a sample of polynucleotide sequences comprising:
contacting under hybridizing conditions said sample of polynucleotide sequences with a composition comprising at least one first and at least one second polynucleotide and detecting said polynucleotide of interest by means of said first detectable marker, the improvements comprising:
(a) said first and second sequences are labeled with a first detectable marker and are either present as separate molecules from which said first polynucleotide sequence has not been isolated or are covalently linked and further characterized in that said first sequence is capable of hybridizing to said sequence of interest and said second sequence is not capable of hybridizing to said sequence of interest and is not capable of hybridizing to said first sequence; and
(b) said sample is further contacted, prior to detecting, with a composition comprising at least one-third polynucleotide sequence that is unlabeled or is labeled with a second detectable marker and characterized in that said third sequence is not capable of hybridizing to said first sequence and is not capable of hybridizing to said sequence of interest, and further characterized in that said third sequence is:
(i) capable of hybridizing to said second sequence, such that by hybridizing to said second sequence said third sequence blocks hybridization between said second sequence and complementary non-target sequences that may be contained in the sample and decreases the likelihood that said second sequence will generate a false positive signal upon detection of said first detectable marker; or
(ii) substantially identical to said second sequence, such that by means of hybridizing to said complementary non-target sequences that may be contained in the sample said third sequence blocks hybridization between said second sequence and said complementary non-target sequences and decreases the likelihood that said second sequence will generate a false positive signal upon detection of said first detectable marker.

13. A method in accordance with claim 12, wherein said first polynucleotide sequence is covalently linked to said second polynucleotide sequence in a chromosome.

14. A method in accordance with claim 13, wherein said first polynucleotide sequence is specific for a polynucleotide sequence selected from the group consisting of *N. gonorrhoea*, herpes simplex virus I, herpes simplex virus II, Brucella abortus, Bordetella pertussis, Shigella dysenteria, Haemophilus influenzae, Mycobacterium tuberculosis, Pseudomonas pseudomallei, Salmonella typhi, Salmonella typhimurium and *N. meningitidis*.

15. A method in accordance with claim 12, wherein said third polynucleotide sequence is from about 50 to about 250 nucleotides in length.

16. A method in accordance with claim 12 wherein said second polynucleotide sequence comprises a vector polynucleotide sequence.

17. A method in accordance with claim 12, wherein said second polynucleotide sequence is a host polynucleotide sequence.

18. A method in accordance with claim 12, wherein said third polynucleotide sequence is present in an amount by weight from about 100 to about 1000 fold greater than said second polynucleotide sequence.

19. A method according to claim 12, wherein said sample is derived from human nucleic acid material.

20. A method according to claim 12, comprising contacting under hybridizing conditions said composition of first and second sequences with at least one of said third sequence, wherein said third sequence is present in an amount by weight that is at least 100 fold greater than the amount by weight of said second sequence and, at about the same time, contacting under hybridizing conditions said composition of first and second sequences with said sample.

21. A method according to claim 12, comprising first contacting under hybridizing conditions said composition of first and second sequences with at least one of said third sequence characterized in that said third sequence is capable of hybridizing to said second sequence, wherein said third sequence is present in an amount by weight that is at least 100 fold greater than the amount by weight of said second sequence, and then, in a second step, contacting under hybridizing conditions said composition of first and second sequences with said sample.

22. A method according to claim 12, comprising first contacting under hybridizing conditions said sample with at least one of said third sequence characterized in that said third sequence is substantially identical to said second sequence, wherein said third sequence is present in an amount by weight that is at least 10 fold greater than the amount by weight of said complementary non-target sequences in the sample, and then, in a second step, contacting under hybridizing conditions said composition of first and second sequences with said sample.

* * * * *